US012614629B2

(12) United States Patent (10) Patent No.: US 12,614,629 B2

Errico et al. (45) Date of Patent: Apr. 28, 2026

(54) METHODS AND SYSTEMS FOR COMMUNICATION BETWEEN SONOGRAPH USERS AND RADIOGRAPH INTERPRETERS

(71) Applicant: KONINKLIJKE PHILIPS N.V., Eindhoven (NL)

(72) Inventors: Claudia Errico, Medford, MA (US); Lucas de Melo Oliveira, Wilmington, MA (US); Deyu Sun, Chicago, IL (US); Jochen Kruecker, Andover, MA (US); Seyedali Sadeghi, Melrose, MA (US); Hua Xie, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 38 days.

(21) Appl. No.: 18/685,962

(22) PCT Filed: Aug. 16, 2022

(86) PCT No.: PCT/EP2022/072800

§ 371 (c)(1),
(2) Date: Feb. 23, 2024

(87) PCT Pub. No.: WO2023/025612

PCT Pub. Date: Mar. 2, 2023

(65) Prior Publication Data

US 2025/0182879 A1 Jun. 5, 2025

Related U.S. Application Data

(60) Provisional application No. 63/236,880, filed on Aug. 25, 2021.

(51) Int. Cl.
*G16H 30/20* (2018.01)
*G16H 30/40* (2018.01)

(52) U.S. Cl.
CPC ............. *G16H 30/20* (2018.01); *G16H 30/40* (2018.01)

(58) Field of Classification Search
CPC ............................... G16H 30/20; G16H 30/40
See application file for complete search history.

(56) References Cited

U.S. PATENT DOCUMENTS

2008/0166070 A1* 7/2008 Kariathungal ......... G16H 30/40
382/305
2008/0249407 A1 10/2008 Hill et al.
(Continued)

FOREIGN PATENT DOCUMENTS

WO 2019197427 A1 10/2019
WO 2020020770 A1 1/2020

OTHER PUBLICATIONS

Madi M, Kumar M, Pentapati KC, Vineetha R. Smart-phone based telemedicine: Instant messaging application as a platform for radiographic interpretations of jaw pathologies. J Oral Biol Craniofac Res. Jul.-Sep. 2021;11(3):368-372. doi: 10.1016/j.jobcr.2021.04.003. Epub Apr. 14, 2021. (Year: 2021).*
(Continued)

*Primary Examiner* — Joshua B Blanchette

(57) ABSTRACT

A method (100) for providing information to a sonograph user, including providing (130) a sonogram atlas comprising one or more sonogram preferences of each of a number of different radiograph interpreters, the sonogram preferences comprising at least one of a preferred view and a measurement for each of a number of sonogram types, receiving (140) a request for information from the sonogram atlas about a sonogram being obtained by a sonograph user from a patient, wherein the request comprises one or more of demographic information about the patient, a type of exam, a reason for imaging, an identification of which of the number of different radiograph interpreters ordered the
(Continued)

sonogram, and an identification of which of the one or more sonogram types was ordered by the identified radiograph interpreter(s) retrieving (150) the one or more sonogram preferences of the identified radiograph interpreter(s).

20 Claims, 5 Drawing Sheets

(56)                 References Cited

U.S. PATENT DOCUMENTS

| 2013/0129165 | A1* | 5/2013 | Dekel | .................... | G16H 30/20 |
| | | | | | 382/128 |
| 2019/0350564 | A1 | 11/2019 | Gajdos et al. | | |
| 2020/0214676 | A1* | 7/2020 | McLaughlin | ......... | G06T 7/0002 |
| 2021/0093301 | A1* | 4/2021 | Wang | .................... | A61B 8/463 |

OTHER PUBLICATIONS

International Search Report and Written Opinion for PCT/EP2022/072800; Mailing date: Dec. 1, 2022, 9 pages.

* cited by examiner

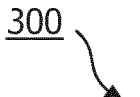
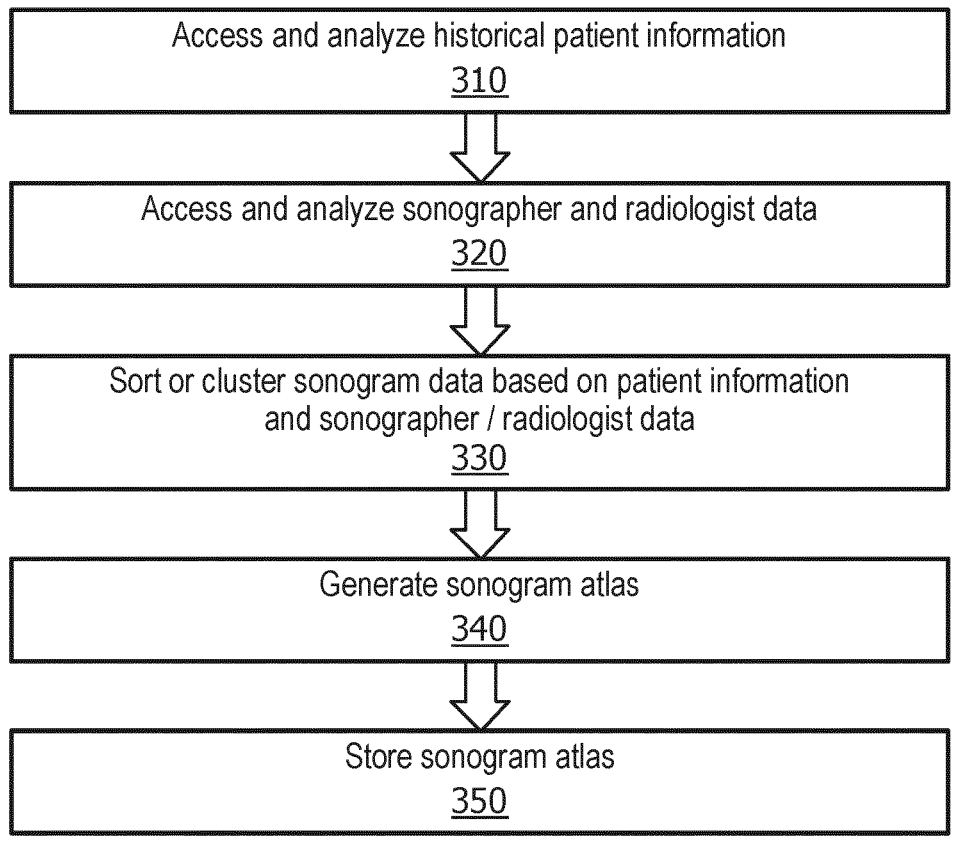
FIG. 3

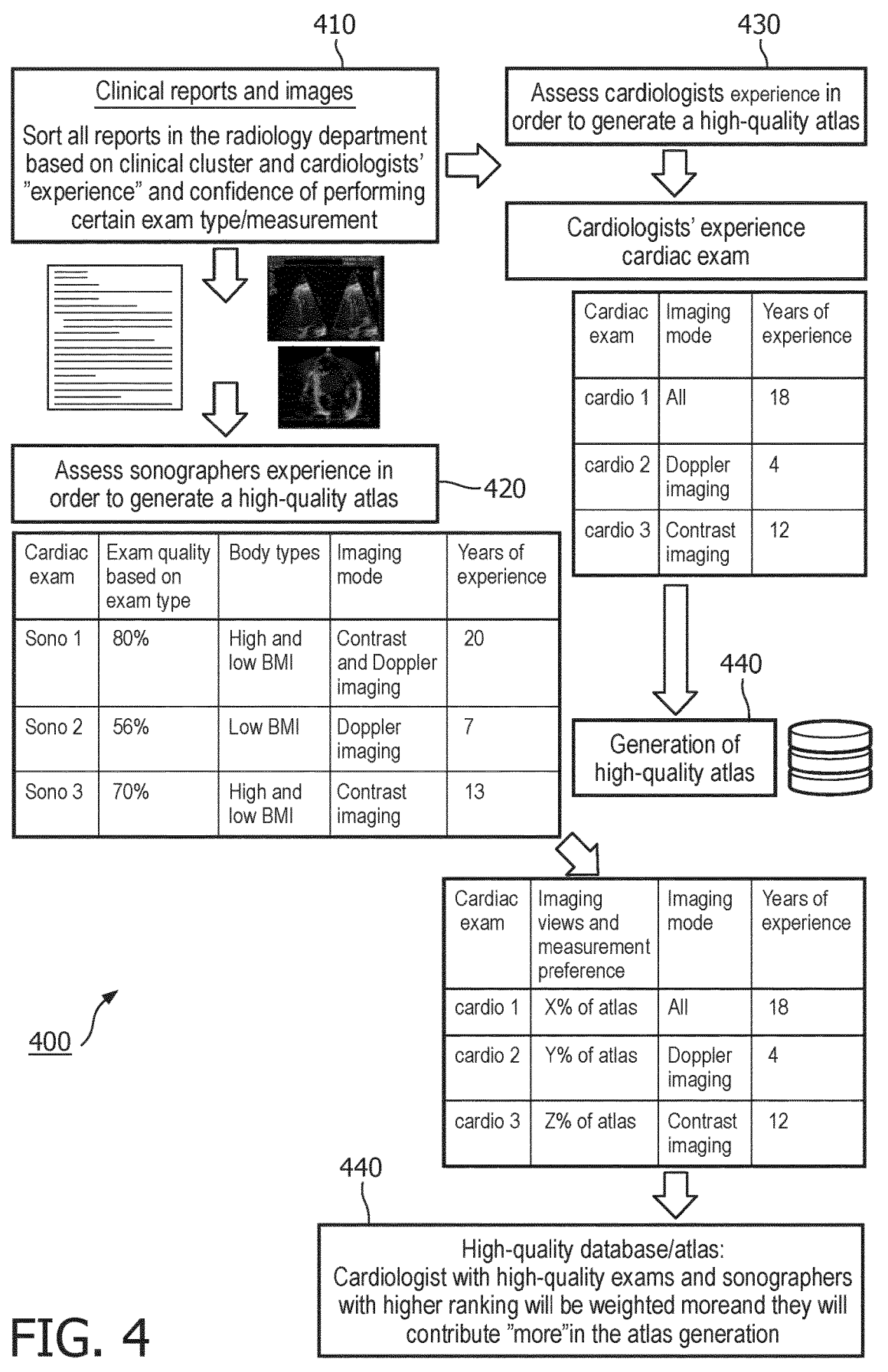

410

430

Clinical reports and images

Sort all reports in the radiology department based on clinical cluster and cardiologists' "experience" and confidence of performing certain exam type/measurement Assess cardiologists experience in order to generate a high-quality atlas Cardiologists' experience cardiac exam

| Cardiac exam | Imaging mode | Years of experience |
|---|---|---|
| cardio 1 | All | 18 |
| cardio 2 | Doppler imaging | 4 |
| cardio 3 | Contrast imaging | 12 |

Assess sonographers experience in order to generate a high-quality atlas

420

| Cardiac exam | Exam quality based on exam type | Body types | Imaging mode | Years of experience |
|---|---|---|---|---|
| Sono 1 | 80% | High and low BMI | Contrast and Doppler imaging | 20 |
| Sono 2 | 56% | Low BMI | Doppler imaging | 7 |
| Sono 3 | 70% | High and low BMI | Contrast imaging | 13 |

440

Generation of high-quality atlas

400

| Cardiac exam | Imaging views and measurement preference | Imaging mode | Years of experience |
|---|---|---|---|
| cardio 1 | X% of atlas | All | 18 |
| cardio 2 | Y% of atlas | Doppler imaging | 4 |
| cardio 3 | Z% of atlas | Contrast imaging | 12 |

440

High-quality database/atlas:
Cardiologist with high-quality exams and sonographers with higher ranking will be weighted moreand they will contribute "more"in the atlas generation

FIG. 4

METHODS AND SYSTEMS FOR COMMUNICATION BETWEEN SONOGRAPH USERS AND RADIOGRAPH INTERPRETERS

CROSS-REFERENCE TO PRIOR APPLICATIONS

This application is the U.S. National Phase application under 35 U.S.C. § 371 of International Application No. PCT/EP2022/072800, filed on Aug. 16, 2022, which claims the benefit of U.S. Provisional Patent Application No. 63/236,880, filed on Aug. 25, 2021. These applications are hereby incorporated by reference herein.

FIELD OF THE DISCLOSURE

The present disclosure is directed generally to methods and systems for improving sonography by providing information to a sonograph user from a sonogram atlas of high-quality sonogram data generated from expert radiograph interpreter(s) and sonograph user(s) data.

BACKGROUND

Sonograph users such as sonographers and radiologists/cardiologists are two major pillars in clinical workflow, and often work together closely to ensure high quality of imaging data, diagnostic findings, and accurate transcription of clinical reports. However, these two roles lack a seamless bi-directional communication platform enabling feedback of data quality.

Depending on the clinical institution they are affiliated with, radiologists/cardiologists may have similar preferences for selecting imaging views within a scanning protocol for quantification and measurements and for generating clinical reports. Similarly, sonograph users follow scanning protocol guidelines to ensure that acquired imaging views, measurements, and overall completeness of the sonogram exam are in-line with the way-of-working of the attending radiologist/cardiologists. To accomplish this, sonograph users may seek approval or help from the radiologist/cardiologist during or after the imaging session. For example, depending on the volume of exams performed during the day, sonograph users may call radiologists into the scanning room to make sure the quality of the ultrasound images, the selected imaging views, and/or performed measurements are in-line with the radiologists/cardiologists' preferences or way of working. This step may be crucial, especially for novice sonograph users, to ensure the exam is complete, fits the quality requirements of the radiologists, and to avoid additional exams for the patient.

However, asking for assistance from the radiologist/cardiologist during or after the imaging session interrupts the workflow of both the sonograph user and the cardiologist. To date, the only way to check the completeness of an exam is by reviewing the protocol checklist: however, there is no quality feedback provided to the sonograph user in real-time. Further, the sonograph user only has access to the attending radiologist/cardiologist of the day, which may not be the radiologist/cardiologist that ordered the sonogram.

SUMMARY OF THE DISCLOSURE

There is a continued need for methods and systems that improve sonography by providing information to a sonograph user from a sonogram atlas of high-quality sonogram data, without interrupting the workflow of either the sonograph user or the radiograph interpreter such as a radiologist or cardiologist. Various embodiments and implementations are directed to a method and system for providing a sonogram atlas of high-quality sonogram data (i.e., views, measurements, and desired way-of working to complete certain imaging exams). A sonogram atlas system includes a sonogram atlas generated by sorting the exam type and the experience of a number of different sonograph users and radiograph interpreters that completed and reviewed that exam, respectively. The atlas contains the sonogram preferences including a preferred view and/or measurement for each of a number of sonogram types. Patient data are collected including at least demographic information about the patient, referral information, an identification of which of the number of different specialists ordered the sonogram, and an identification of which of the one or more sonogram types was ordered along with which scanning protocol will be followed. The system retrieves, from the sonogram atlas based on the request, the one or more sonogram preferences retrieved from a list of experienced radiograph interpreters, and provides, to the sonograph user via a user interface of the sonogram atlas system, the retrieved one or more sonogram preferences of the identified radiograph interpreter.

According to an embodiment, the system includes an atlas of imaging views and measurements by reading radiologist/cardiologists' reports based on patients' population, disease, and reason for imaging, and analyzing the radiologist/cardiologists' way of working within each medical institution and/or radiology department. By doing so, the system includes a smart agent able to generate an atlas of selected and preferred imaging views that the group of radiologists/cardiologists within the institution are most likely to label high-quality, and would use to perform measurements and generate reports. This information can be leveraged by sonograph users during future scanning sessions.

For example, the sonogram atlas system could help sonograph users respond to a question such as "what would the cardiologist prefer, request, or do?" with virtual feedback. According to an embodiment, the system is not specifically tailored to one single attending radiologist/cardiologist, thereby avoiding bias. Rather, the virtual collaboration comes from gathering feedback from the entire population of radiologists/cardiologists working within the medical facility.

According to an aspect, a method for providing information to a sonograph user using a sonogram atlas system is provided. The method includes: (i) providing a sonogram atlas including one or more sonogram preferences of each of a number of different radiograph interpreters, the sonogram preferences including a preferred view and/or measurement for each of a number of sonogram types: (ii) receiving, from a sonograph user, a request for information from the sonogram atlas about a sonogram being obtained by the sonograph user from a patient, wherein the request includes one or more of demographic information about the patient, a type of exam, a reason for imaging, a reason for referral and imaging, and an identification of which of the one or more sonogram types was ordered by the identified radiograph interpreter(s): (iii) retrieving, from the sonogram atlas based on the request, the one or more sonogram preferences of the identified expert radiograph interpreter(s); and (iv) providing, to the sonograph user via a user interface of the sonogram atlas system, the retrieved one or more sonogram preferences of the identified radiograph interpreter.

According to an embodiment, the method further includes adjusting, based on the provided retrieved information, a parameter of the sonogram being obtained by the sonograph user from the patient.

According to an embodiment, providing the retrieved one or more sonogram preferences of the identified radiograph interpreter to the sonograph user via the user interface includes displaying one or more sonogram images.

According to an embodiment, providing the retrieved one or more sonogram preferences of the identified radiograph interpreter to the sonograph user via the user interface includes information about one or more sonogram preferences for each of a number of radiograph interpreters.

According to an embodiment, the method further includes receiving, from the sonograph user after receiving the provided retrieved information, a request to communicate with the identified radiograph interpreter; and establishing, in response to the request, communication between the sonograph user and the identified radiograph interpreter.

According to an embodiment, the sonogram atlas is generated by a method including: (i) clustering a number of historical patients with sonogram data into similar clusters, wherein similarity is based on at least: demographics for the patients and a sonogram type for the patient sonogram data: (ii) identifying a number of different radiograph interpreters, wherein identifying further includes, for each of the number of different radiograph interpreters, identifying years of experience, a radiology experience level, a specialty in which the radiograph interpreters are considered experts, and identifying a number of different sonograph users, wherein identifying further includes, for each of the number of different sonograph users, identifying years of experience, an imaging experience level based on one or more of the type of exam and quality of exams previously completed: (iii) sorting the sonogram data for the number of historical patients based at least in part on the identified years of experience and experience level for the radiograph interpreter associated with the sonogram data, and based at least in part on the identified years of experience and experience level for the sonograph user associated with the sonogram data: (iv) generating, from the sorted sonogram data, the sonogram atlas, wherein the sonogram data associated with radiograph interpreters with more years of experience and higher experience level, and the sonogram data associated with sonograph users with more years of experience and higher experience level (based on, for example, the exam type and success/high quality of data/exams completed over the years), is ranked higher or more reliable than sonogram data associated with radiograph interpreters with fewer years of experience and lower experience level, and the sonogram data associated with sonograph users with fewer years of experience and lower experience level, and further wherein the generated sonogram atlas includes one or more sonogram preferences for each of the number of different radiograph interpreters based on the ranked sonogram data, the sonogram preferences including a preferred view and/or measurement for each of a number of sonogram types. According to an embodiment, the method further includes identifying high-quality sonogram data for each of the number of sonogram types among the sonogram data associated with the historical patients, wherein the step of generating the sonogram atlas is further based in part on the identified high-quality sonogram data. According to an embodiment, the method further includes the step of storing the generated sonogram atlas in a database of the sonogram atlas system.

According to a second aspect is a system configured to provide information to a sonograph user. The system includes: a sonogram atlas including one or more sonogram preferences of each of a number of different radiograph interpreters, the sonogram preferences including a preferred view and/or measurement for each of a number of sonogram types: a user interface configured to receive, from a sonograph user, a request for information from the sonogram atlas about a sonogram being obtained by the sonograph user from a patient, wherein the request includes at least demographic information about the patient, an identification of which of the number of different radiograph interpreters ordered the sonogram, and an identification of which of the one or more sonogram types was ordered by the identified radiograph interpreter; and a processor configured to: (i) retrieve, from the sonogram atlas based on the request, the one or more sonogram preferences of the identified radiograph interpreter; and (ii) direct the user interface to provide the retrieved one or more sonogram preferences of the identified radiograph interpreter.

According to an embodiment, the processor is further configured to: receive, from the sonograph user after receiving the provided retrieved information, a request to communicate with the identified radiograph interpreter; and establish, in response to the request, communication between the sonograph user and the identified radiograph interpreter.

According to an embodiment, the user interface is configured to receive the request to communicate from the sonograph user, and further the user interface is configured to facilitate the established communication between the sonograph user and the identified radiograph interpreter.

According to an embodiment, the sonogram atlas is generated by: (i) clustering a number of historical patients with sonogram data into similar clusters: (ii) identifying a number of different radiograph interpreters and a number of different sonograph users: (iii) sorting the sonogram data based on the identified number of different radiograph interpreters and/or identified number of different sonograph users: (iv) generating the sonogram atlas from the sorted sonogram data; and (v) storing the generated sonogram atlas in storage.

According to an embodiment, the system is configured to receive, from the sonograph user based on the provided retrieved information, an adjustment of one or more parameters of the sonogram being obtained by the sonograph user from the patient.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. The figures showing features and ways of implementing various embodiments and are not to be construed as being limiting to other possible embodiments falling within the scope of the attached claims. Also, the drawings are not necessarily to scale, emphasis instead generally being placed upon illustrating the principles of the various embodiments.

FIG. 3 is a flowchart of a method for generating a sonogram atlas, in accordance with an embodiment.

FIG. 4 is a schematic representation of a process for generating a sonogram atlas, in accordance with an embodiment.

DETAILED DESCRIPTION OF EMBODIMENTS

The present disclosure describes various embodiments of a system and method configured to provide high-quality information to a sonograph user using a sonogram atlas system. More generally, Applicant has recognized and appreciated that it would be beneficial to provide a method and system to enable communication between sonograph users and radiograph interpreters, without interrupting workflow. The system includes a sonogram atlas including one or more sonogram preferences of each of a number of different radiograph interpreters and sonograph users, the sonogram preferences including a preferred view and/or measurement for each of a number of sonogram types. The system receives, from a sonograph user, a request for information from the sonogram atlas about a sonogram being obtained by the sonograph user from a patient, the request including at least demographic information about the patient, an identification of which of the number of different radiograph interpreters ordered the sonogram, and an identification of which of the one or more sonogram types was ordered by the identified radiograph interpreter. The system retrieves, from the sonogram atlas based on the request, the one or more sonogram preferences of the identified radiograph interpreter, and provides, to the sonograph user via a user interface of the sonogram atlas system, the retrieved one or more sonogram preferences of the identified radiograph interpreter.

The embodiments and implementations disclosed or otherwise envisioned herein can be utilized with any imaging or monitoring system, including but not limited to medical devices or systems. For example, one application of the embodiments and implementations herein is to improve ultrasound machines, such as, e.g., the Philips® EPIQ or Affiniti ultrasound devices (manufactured by Koninklijke Philips, N.V.), among other products. Another application of the embodiments and implementations herein is to improve medical monitoring systems such as, e.g., a Philips Patient Monitoring system such as the Philips IntelliSpace® Precision Medicine products (manufactured by Koninklijke Philips, N.V.), among many other products. However, the disclosure is not limited to these devices or systems, and thus disclosure and embodiments disclosed herein can encompass any imaging or monitoring system.

Figure 1:
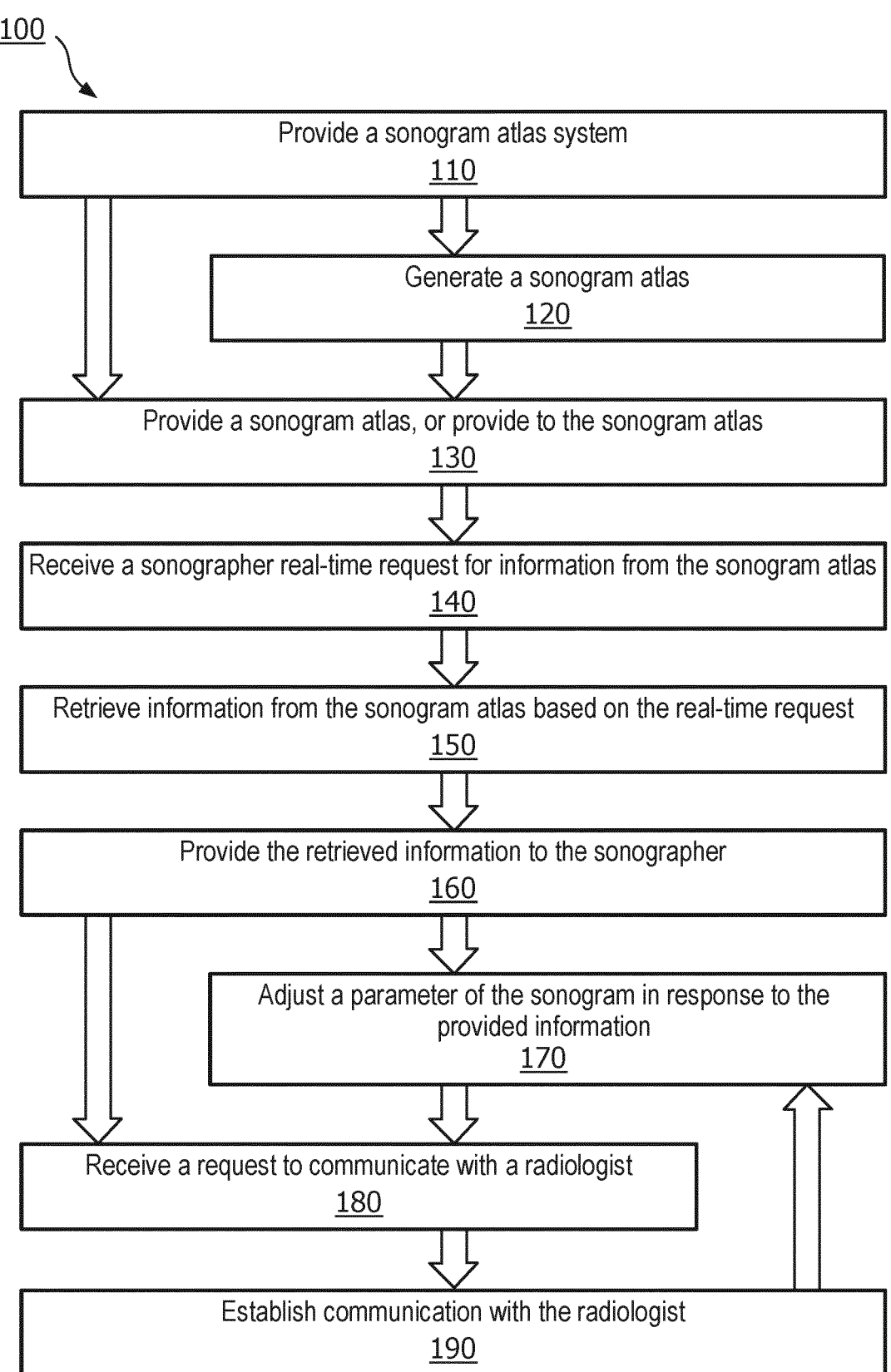
FIG. 1 is a flowchart of a method for providing information to a sonograph user using a sonogram atlas system, in accordance with an embodiment.

Referring to FIG. 1, in one embodiment, is a flowchart of a method 100 for providing information to a sonograph user using a sonogram atlas system. The methods described in connection with the figures are provided as examples only, and shall be understood not to limit the scope of the disclosure. The sonogram atlas system can be any of the systems described or otherwise envisioned herein. The sonogram atlas system can be a single system or multiple different systems.

Figure 2:
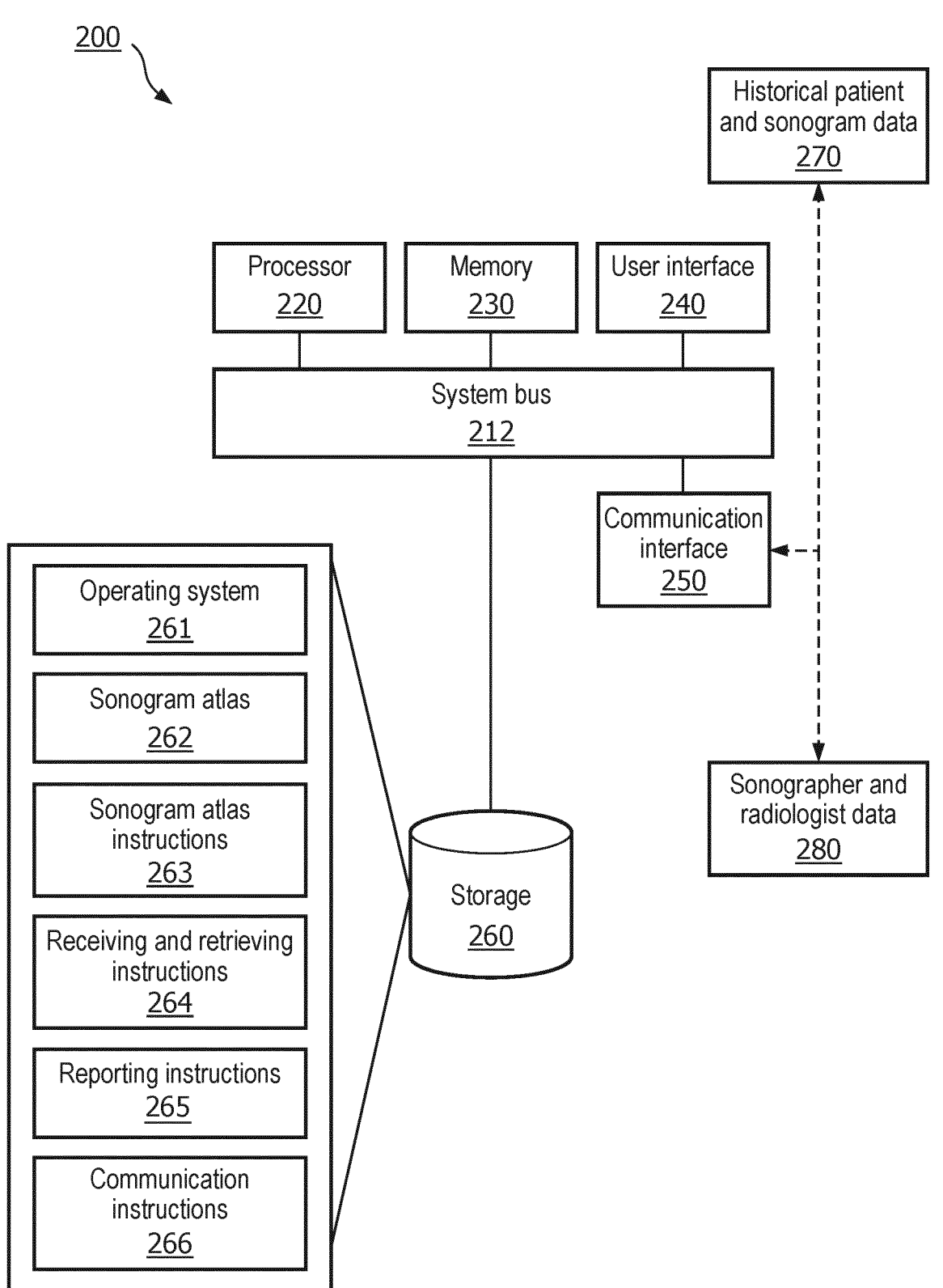
FIG. 2 is a schematic representation of a sonogram atlas system, in accordance with an embodiment.

At step 110 of the method, a sonogram atlas system 200 is provided. Referring to an embodiment of a sonogram atlas system 200 as depicted in FIG. 2, for example, the system includes one or more of a processor 220, memory 230, user interface 240, communications interface 250, and storage 260, interconnected via one or more system buses 212. It will be understood that FIG. 2 constitutes, in some respects, an abstraction and that the actual organization of the components of the system 200 may be different and more complex than illustrated. Additionally, monitoring system 200 can be any of the systems described or otherwise envisioned herein. Other elements and components of the sonogram atlas system 200 are disclosed and/or envisioned elsewhere herein.

According to an embodiment, the sonogram atlas system includes or is in direct or indirect communication with historical patient and sonogram data 270, such as a database of historical patient and sonogram data. The historical patient and sonogram data includes, among other possible data, information such as demographics about a number of patients, along with sonogram data for the sonograms obtained for the number of patients. The database of historical patient and sonogram data can be any such database, including but not limited to the databases and systems described or otherwise envisioned herein.

According to an embodiment, the sonogram atlas system includes or is in direct or indirect communication with sonograph user and radiograph interpreter data 280, such as a database of sonograph user and radiograph interpreter data. The sonograph user and radiograph interpreter data includes, among other possible data, information such as experience level, years of experience, historical sonograph data, sonogram preferences, and other data about sonograph users and radiograph interpreters. The database of sonograph user and radiograph interpreter data can be any such database, including but not limited to the databases and systems described or otherwise envisioned herein.

At step 120 of the method, a sonogram atlas is generated. The sonogram atlas includes, among other possible information, sonogram preferences for each of a number of different radiograph interpreters, such as the different radiograph interpreters that work for or with the care facility or other entity where the sonogram atlas is provided, housed, or otherwise found. According to an embodiment, sonogram preferences include one or more preferred views and/or measurements for each of a number of different sonogram types or sonogram requests. According to an embodiment, the sonogram atlas includes ranked sonogram data, where sonogram data associated with radiograph interpreters with more years of experience and higher experience level (based on, for example, exam type and success/high quality of data/exams historically completed), and/or sonogram data associated with sonograph users with more years of experience and higher experience level, is ranked higher or more reliable than sonogram data associated with radiograph interpreters with fewer years of experience and lower experience level, and/or the sonogram data associated with sonograph users with fewer years of experience and lower experience level.

According to an embodiment, the sonogram atlas is generated in whole or in part using a machine learning algorithm that obtains data such as historical patient demographic data: patient sonogram data: radiograph interpreter data such as identity, experience, and preferences; sonograph user data such as identity, experience, and preferences; and a wide variety of other data. Generation of the sonogram atlas is described elsewhere herein, including with regard to method 300 in FIG. 3, although other methods of generating the sonogram atlas are possible. Thus, the sonogram atlas can include any data or information described or otherwise envisioned herein.

According to an embodiment, the sonogram atlas system includes a machine learning algorithm that can identify and/or select preferences of different radiograph interpreters/cardiologists within the institution based factors such as a patient's disease(s), the reason for imaging (i.e. referral from care giver), a current selected scanning protocol (i.e. cardiac ultrasound imaging), clinical measurements (such as, for example, to contour and measure heart chambers), the radiograph interpreters/cardiologists' years of experience and confidence with performing various measurements, among other data. The approach can leverage the use of an integrated platform where patient data, imaging protocols, quantification measurements, and/or clinical reports can be accessed. This data may be real-time data or historical data, for example.

Once the sonogram atlas is generated, it can be utilized immediately or stored in local or remote storage for use in further steps of the method, such as by radiograph interpreters and/or sonograph users.

At step 130 of the method, the generated sonogram atlas or access to the sonogram atlas is provided. This can include, for example, providing access to a sonogram atlas or sonogram atlas system through a user interface. The user interface may be a dedicated component of the sonogram atlas system, or the user interface may be in communication with various systems including but not limited to the sonogram atlas system. For example, a sonograph user obtaining sonogram data can access the sonogram atlas or sonogram atlas system via a user interface of the imaging equipment, or through a different user interface such as that of a computer or other device or system. As one example, the sonograph user may obtain access to the sonogram atlas or sonogram atlas system via a handheld device such as a tablet, smartphone, or other device.

At step 140 of the method, the sonograph user accesses the sonogram atlas system and submits a request for information. According to an embodiment, the sonograph user is obtaining sonogram data from a patient and submits the request for information, such as through a button, touchscreen, or any other user interface or mechanism. Thus, the sonogram atlas system receives a request for information from the sonogram atlas about a sonogram being obtained by the sonograph user from a patient. According to an embodiment, the request includes at least demographic information about the patient for whom the sonogram is being performed, an identification of who at the facility ordered the sonogram, and an identification of which of one or more different sonogram types was successfully reviewed by the identified radiograph interpreter and is being obtained by the sonograph user. This information may be submitted by manually entering the information, by selecting the data in a user interface, or may be automatically gathered by and/or transmitted to the system in response to a request by the sonograph user.

At step 150 of the method, the sonogram atlas system retrieves information from the sonogram atlas based on the request received from the sonograph user. The information retrieved from the sonogram atlas can be any information relevant to the request and/or relevant to the submitted information such as demographic information about the patient for whom the sonogram is being performed, the identification of which of the number of different radiograph interpreters at the facility ordered the sonogram, and the identification of which of one or more different sonogram types was ordered by the identified radiograph interpreter and is being obtained by the sonograph user. For example, the information may be information about the patient, information about the radiograph interpreter such as one or more sonogram preferences of the identified radiograph interpreter, information about the sonograph user, and/or information about a sonogram type, among other possible information. According to an embodiment, the information can be sonogram information or preferences for a number of different radiograph interpreters.

At step 160 of the method, the sonogram atlas system provides the retrieved information to the sonograph user via a user interface such as a user interface of the sonogram atlas system. The information provided to the sonograph user can be any of the information retrieved in response to the request from the sonograph user. For example, the provided information can be information such as one or more sonogram preferences (i.e., imaging view for a specific quantification measurement) of an identified radiograph interpreter, or of a number of different radiograph interpreters. As another example, the provided information can be a sonogram image. The provided information can be any information of the sonogram atlas as described or otherwise envisioned herein.

At optional step 170 of the method, the sonograph user adjusts one or more parameters of the sonogram being obtained by the sonograph user from the patient, in response to the provided retrieved information. For example, the sonograph user may discover one or more preferences of a radiograph interpreter or expert sonograph user, such as a preferred view and/or measurement for the sonogram type being obtained, and may then adjust the method or approach currently being used to align more closely with the preferred view and/or measurement for the radiograph interpreter and sonogram type. Many other adjustments or modifications of the sonogram are possible.

At optional step 180 of the method, after receiving the provided retrieved information, the sonograph user may submit a request to communicate with a radiograph interpreter such as the radiograph interpreter that ordered the requested sonogram, or another radiograph interpreter. Accordingly, the sonogram atlas system receives a request from the sonograph user for virtual communication with an identified radiograph interpreter. The request may be submitted through, and thus received by, a user interface. The user interface may be a dedicated component of the sonogram atlas system, or the user interface may be in communication with various systems including but not limited to the sonogram atlas system. For example, a sonograph user obtaining sonogram data can access the sonogram atlas system and request communication via a user interface of the imaging equipment, or can request communication through a different user interface such as that of a computer or other device or system. As one example, the sonograph user may request communication with a radiograph interpreter through the sonogram atlas system via a handheld device such as a tablet, smartphone, or other device. The request for communication may be to obtain more information, to request clarification, to ask a question, or for any other purpose.

At optional step 190 of the method, the sonogram atlas system establishes communication between the sonograph user and the identified radiograph interpreter in response to the received request. This may occur, for example, after the sonogram atlas system has reached out to the radiograph interpreter to check for availability and received confirmation of availability. For example, the system may send a communication request to the identified radiograph interpreter and wait a certain amount of time for a response. If the system receives a response that the radiograph interpreter is available and willing to communicate, the system can connect the sonograph user and the radiograph interpreter for communication. For example, the communication may be audio, audio and video, text-based, or any other type of communication. The communication may be established using any method for communicating.

Referring to FIG. 2 is a schematic representation of a sonogram atlas system 200. System 200 may be any of the systems described or otherwise envisioned herein, and may include any of the components described or otherwise envisioned herein. It will be understood that FIG. 2 constitutes, in some respects, an abstraction and that the actual organization of the components of the system 200 may be different and more complex than illustrated.

According to an embodiment, system 200 includes a processor 220 capable of executing instructions stored in memory 230 or storage 260 or otherwise processing data to, for example, perform one or more steps of the method. Processor 220 may be formed of one or multiple modules. Processor 220 may take any suitable form, including but not limited to a microprocessor, microcontroller, multiple microcontrollers, circuitry, field programmable gate array (FPGA), application-specific integrated circuit (ASIC), a single processor, or plural processors.

Memory 230 can take any suitable form, including a non-volatile memory and/or RAM. The memory 230 may include various memories such as, for example L1, L2, or L3 cache or system memory. As such, the memory 230 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of system 200. It will be apparent that, in embodiments where the processor implements one or more of the functions described herein in hardware, the software described as corresponding to such functionality in other embodiments may be omitted.

User interface 240 may include one or more devices for enabling communication with a user. The user interface can be any device or system that allows information to be conveyed and/or received, and may include a display, a mouse, and/or a keyboard for receiving user commands. In some embodiments, user interface 240 may include a command line interface or graphical user interface that may be presented to a remote terminal via communication interface 250. The user interface may be located with one or more other components of the system, or may located remote from the system and in communication via a wired and/or wireless communications network.

Communication interface 250 may include one or more devices for enabling communication with other hardware devices. For example, communication interface 250 may include a network interface card (NIC) configured to communicate according to the Ethernet protocol. Additionally, communication interface 250 may implement a TCP/IP stack for communication according to the TCP/IP protocols. Various alternative or additional hardware or configurations for communication interface 250 will be apparent.

Storage 260 may include one or more machine-readable storage media such as read-only memory (ROM), random-access memory (RAM), magnetic disk storage media, optical storage media, flash-memory devices, or similar storage media. In various embodiments, storage 260 may store instructions for execution by processor 220 or data upon which processor 220 may operate. For example, storage 260 may store an operating system 261 for controlling various operations of system 200.

It will be apparent that various information described as stored in storage 260 may be additionally or alternatively stored in memory 230. In this respect, memory 230 may also be considered to constitute a storage device and storage 260 may be considered a memory. Various other arrangements will be apparent. Further, memory 230 and storage 260 may both be considered to be non-transitory machine-readable media. As used herein, the term non-transitory will be understood to exclude transitory signals but to include all forms of storage, including both volatile and non-volatile memories.

While system 200 is shown as including one of each described component, the various components may be duplicated in various embodiments. For example, processor 220 may include multiple microprocessors that are configured to independently execute the methods described herein or are configured to perform steps or subroutines of the methods described herein such that the multiple processors cooperate to achieve the functionality described herein. Further, where one or more components of system 200 is implemented in a cloud computing system, the various hardware components may belong to separate physical systems. For example, processor 220 may include a first processor in a first server and a second processor in a second server. Many other variations and configurations are possible.

According to an embodiment, system 200 includes or is in direct or indirect communication with historical patient and sonogram data 270, such as a database of historical patient and sonogram data. The historical patient and sonogram data includes, among other possible data, information such as demographics about a number of patients, along with sonogram data for the sonograms obtained for the number of patients. The database of historical patient and sonogram data can be any such database, including but not limited to the databases and systems described or otherwise envisioned herein.

According to an embodiment, system 200 includes or is in direct or indirect communication with sonograph user and radiograph interpreter data 280, such as a database of sonograph user and radiograph interpreter data. The sonograph user and radiograph interpreter data includes, among other possible data, information such as experience level, years of experience, historical sonograph data, sonogram preferences, and other data about sonograph users and radiograph interpreters. The database of sonograph user and radiograph interpreter data can be any such database, including but not limited to the databases and systems described or otherwise envisioned herein.

According to an embodiment, storage 260 of system 200 may store one or more algorithms, modules, and/or instructions to carry out one or more functions or steps of the methods described or otherwise envisioned herein. For example, storage 260 may include, among other instructions or data, a sonogram atlas 262, sonogram atlas instructions 263, receiving and retrieving instructions 264, reporting instructions 265, and/or communication instructions 266.

According to an embodiment, sonogram atlas 262 includes information that can be utilized by a sonograph user. For example, the sonogram atlas can include, among other possible information, sonogram preferences for each of a number of different radiograph interpreters and sonograph users, such as the different radiograph interpreters and sonograph users that work for or with the care facility where the sonogram atlas is provided, housed, or otherwise found. According to an embodiment, sonogram preferences include one or more preferred views and/or measurements for each of a number of different sonogram types or sonogram requests. According to an embodiment, the sonogram atlas includes ranked sonogram data, where sonogram data associated with radiograph interpreters with more years of experience and higher experience level, and/or sonogram data associated with sonograph users with more years of experience and higher experience level, is ranked higher or more reliable than sonogram data associated with radiograph interpreters with fewer years of experience and lower experience level, and/or the sonogram data associated with sonograph users with fewer years of experience and lower experience level.

According to an embodiment, sonogram atlas instructions 263 direct the system to generate and/or update or otherwise establish the sonogram atlas 262. According to an embodiment, the sonogram atlas is generated in whole or in part using a machine learning algorithm that obtains data such as historical patient demographic data: patient sonogram data: radiograph interpreter data such as identity, experience, and preferences: sonograph user data such as identity, experience, and preferences; and a wide variety of other data. Generation of the sonogram atlas is described elsewhere herein, including with regard to method 300 in FIG. 3, although other methods of generating the sonogram atlas are possible. Thus, the sonogram atlas can include any data or information described or otherwise envisioned herein. Once the system generates the sonogram atlas, it can be utilized immediately or stored in local or remote storage for use in further steps of the method, such as by radiograph interpreters and/or sonograph users.

According to an embodiment, receiving and retrieving instructions 264 direct the system to receive a request for information from the sonogram atlas 262 about a sonogram being obtained by the sonograph user from a patient. The request may be received via the user interface of system 200. The receiving and retrieving instructions 264 also direct the system to retrieve information from the sonogram atlas based on the request received from the sonograph user. The information retrieved from the sonogram atlas can be any information relevant to the request and/or relevant to the submitted information.

According to an embodiment, reporting instructions 265 direct the system to provide the retrieved information to the sonograph user via a user interface such as user interface 240 of the sonogram atlas system. The provided information can be any information of the sonogram atlas as described or otherwise envisioned herein. The system may provide the information to a user via any mechanism, including but not limited to a visual display, an audible notification, a text message, an email, a page, or any other method of notification.

According to an embodiment, communication instructions 266 direct the system to establish communication between a sonograph user and a radiograph interpreter in response to a request received from a sonograph user.

Accordingly, the sonogram atlas system receives a request from the sonograph user for communication with an identified radiograph interpreter. The request may be submitted through, and thus received by, a user interface. The user interface may be a dedicated component of the sonogram atlas system, or the user interface may be in communication with various systems including but not limited to the sonogram atlas system. To connect the parties, the system may send a virtual communication request to the radiograph interpreter and wait a certain amount of time for a response. If the system receives a response that the radiograph interpreter is available and willing to communicate, the system can connect the sonograph user and the radiograph interpreter for communication. For example, the communication may be audio, audio and video, text-based, or any other type of communication. The communication may be established using any method for communicating. Alternatively, if the radiograph interpreter fails to respond or indicates that they are unavailable, the system can notify the sonograph user and can attempt to establish communication again either immediately or at a future time.

Referring to FIG. 3, in one embodiment, is a method 300 for generating a sonogram atlas 262. According to an embodiment, the sonogram atlas is generated in whole or in part using a machine learning algorithm that obtains data such as historical patient demographic data: patient sonogram data: radiograph interpreter data such as identity, experience, and preferences; sonograph user data such as identity, experience, and preferences; and a wide variety of other data. The sonogram atlas can include any data or information described or otherwise envisioned herein.

At step 310 of method 300, the sonogram atlas system accesses and/or otherwise retrieves or receives patient information, including information about patients from prior, historical imaging or medical treatment. The patient information can include any information about each of a number of patients, including but not limited to demographic information, body type (such as BMI), pre-existing health conditions, current health conditions, reason for imaging, prior ultrasound or other imaging, and imaging mode (such as Doppler, contrast imaging, etc.) for imaging obtained for the patient.

Also at step 310 of the method, the sonogram atlas system processes and analyses the accessed or received patient information. For example, the sonogram atlas system extracts relevant information from the patient information, such as through natural language processing and/or any other method for data or feature identification and/or extraction. According to an embodiment, the system also uses natural language processing to build the quality of the atlas, as reports often include hints from the radiograph interpreters about completeness and quality of images, measurements, and exams. According to an embodiment, the system clusters the number of patients into one or more clusters based on one or more features such as demographics, reason for referral, pre-existing health conditions, body type, and/or pre-existing imaging data, among other possible features. The clusters can then be used to extract respective clinical reports to analyze the way-of-working and style preferences of radiograph interpreters.

According to an embodiment, the sonogram atlas system includes a machine learning algorithm that performs some or all of the functions at step 310 of the method.

At step 320 of the method, the sonogram atlas system accesses and/or otherwise retrieves or receives sonograph user and radiograph interpreter data. The sonograph user and radiograph interpreter data can include, among other possible data, information such as experience level, years of experience, historical sonograph data, sonogram preferences, imaging modality specialty (i.e., cardiac imaging and vascular imaging), and other data about sonograph users and radiograph interpreters. The sonograph user and radiograph interpreters experience levels are utilized to generate a high-quality atlas. According to an embodiment, experience can be based one or more of: (i) quality of imaging exams, which can be utilized if/when radiograph interpreters assign an exam quality score or other feedback for an exam: (ii) years of experience: (iii) ability to obtain standard and complex view for a certain imaging protocols and diseases: (iv) experience with certain types of exams; and other data. Among other possible embodiments, the sonograph user and radiograph interpreter data can include the ultrasound technology utilized by the sonograph users and/or radiograph interpreters. For example, the data can include information about the sonograph users' and/or radiograph interpreters' experience with ultrasound machines, ultrasound transducers, ultrasound processing software, or any other component or element of ultrasound technology available to or utilized by the sonograph users and/or radiograph interpreters.

According to an embodiment, sonograph user and radiograph interpreter data is also utilized or otherwise analyzed to identify high-quality sonogram images. For example, the system may include sonogram data associated with sonograph users and radiograph interpreters, and the system can list or associate sonograph users and radiograph interpreters associated with high-quality sonogram data. High-quality, for example, can mean sonogram data with accurate imaging, measurements, and/or other parameters, among other definitions. In some circumstances, a sonograph user may encounter challenges during scanning exams and some of the acquired images and/or performed measurements might not be of high quality, especially if the patient is challenging, unwell, and/or the sonograph user is a novice, among other reasons. Images labeled as poor or including poor quality from inconclusive and/or incomplete exams from inexperienced/novice or experienced sonograph users won't be considered for inclusion in the atlas. For example, in order to avoid polluting the atlas with images from poor quality measurements or inconclusive exams, sonograph users and/or radiograph interpreters can be ranked based on experience and clinical outcome (i.e., incomplete exam due to high BMI, among many other reasons). In contrast, sonograph users and radiograph interpreters associated with high-quality exams have higher ranking and will be weighted higher and they will contribute more to the atlas generation.

According to an embodiment, therefore, the system can include a data, such as a database, including preferred images, frames, and/or reports that are labeled as high-quality from a radiograph interpreter or sonograph user and were used to perform measurements and generate clinical reports. For example, the system can use natural language processing (NLP) to generate a dictionary of findings and quality of the imaging exams (i.e., test=mitral valve regurgitation, quality=high quality). The system can also utilize view recognition on images that were utilized to generate clinical reports. If the radiograph interpreters label images as high-quality and the exam is labeled as complete, these views can then populate an atlas of preferred views. The system can also utilize a machine learning algorithm to learn annotation, segmentation, and landmarks contouring styles, such as preferred annotation, segmentation, and landmarks contouring styles for each of one or more radiograph interpreters.

According to an embodiment, the high-quality database of images and measurements is based on patient population radiograph interpreter and sonograph user styles and imaging preferences, and can be generated by utilizing deep learning networks, such as landmark localization or image classification. Thus, NLP can be utilized to extract from the reports and/or images/measurements available on a system: (i) exam quality; and (ii) a dictionary of diseases, pathologies, and diagnosis, which will be useful to further populate the high-quality atlas with images and measurements that lead to successful exams. The purpose of the atlas is to create a database of high-quality imaging views that radiograph interpreters are likely to select and prefer to use for quantification measurements and reporting. This atlas then can be used by sonograph users during a virtual collaboration request. The approach gives sonograph users the possibility to consult not only attending radiograph interpreters, but the entire group of specialists within the institution.

As just one example, cardiac views for certain diseases and measurements can be standardized by looking across patients and across radiograph interpreters' preferences. For example, when measuring ejection fraction, different cardiologists have different preferences. Some cardiologists prefer contrast images because there is a clear boundary of the left ventricle, while other cardiologists prefer a regular four-chamber image. The method and system disclosed herein can select by disease and cardiac landmarks, which are the most common cardiac views cardiologists tend to choose for patient's reports.

At step 330 of the method, clinical reports or other sonogram data are analyzed and sorted. The analysis or sorting is based on one or more of patient information, such as the clinical clusters formed at step 310, and/or on sonograph user/radiograph interpreter experience and confidence in performing a certain exam type/measurement, such as the analysis performed at step 320. According to an embodiment, step 330 is automatically performed by the system.

At step 340, the sonogram atlas is generated using one or more of the clustered patient information, the clustered or sorted/ranked sonograph user and radiograph interpreter data, and the sorted clinical reports or other sonogram data. Once completed, the sonogram atlas includes a database of high-quality sonogram data that is associated with both relevant patient information (such as sonogram type and reason for the sonogram), and with relevant radiograph interpreter information (such as which radiograph interpreter includes which preferences or sonogram parameters). At step 350 of the method, the generated sonogram atlas is stored in local or remote storage for use by the sonogram atlas system. According to an embodiment, steps 340 and 350 are automatically performed by the system.

Referring to FIG. 4, in one embodiment, is a schematic representation of a process 400 for generating a sonogram atlas. The process includes an approach for evaluating sonograph user and radiograph interpreter experience and atlas generation. The example shown by FIG. 4 can be extended and generalized to other type of exams (i.e. abdominal exam and radiograph interpreters). In process 400, at step 410 clinical reports and images are sorted based on clinical cluster and sonograph user/radiograph interpreter experience, including the sonograph user's confidence in performing exam types or measurements, among other possible sorting bases. At step 420, the system assesses sonograph user experience to facilitate generation of a high-quality atlas. For example, the analysis of sonograph user experience can include information about examination quality based on examination type, experience with body type (based on, for example, BMI among other body quantifications), imagine mode (such as contrast imaging, Doppler imaging, and other imaging types), and years of experience, among other experience quantifiers. At step 430, the system assesses radiograph interpreter experience to facilitate generation of a high-quality sonogram atlas. For example, the analysis of radiograph interpreter experience can include experience with imaging mode (such as contrast imaging, Doppler imaging, and other imaging types), and years of experience, among other experience quantifiers. At step 440, the system generates a high-quality atlas using information from steps 410 through 430. The atlas may utilize, for example, information for each radiograph interpreter such as imaging views and measurement preferences for one or more imaging modes, years of experience, and more, such that at 450, the atlas may include data from sonograph users and/or radiograph interpreters with more high-quality exams. For example, sonograph users and/or radiograph interpreters with high-quality exams and/or higher ranking can be weighted more and can contribute more to the atlas generation. For example, the table at 440 in FIG. 4 includes information about the percentage of the atlas contributed by each radiograph interpreter (e.g., cardiologist #1 contributes X % of the atlas, etc.).

Figure 5:
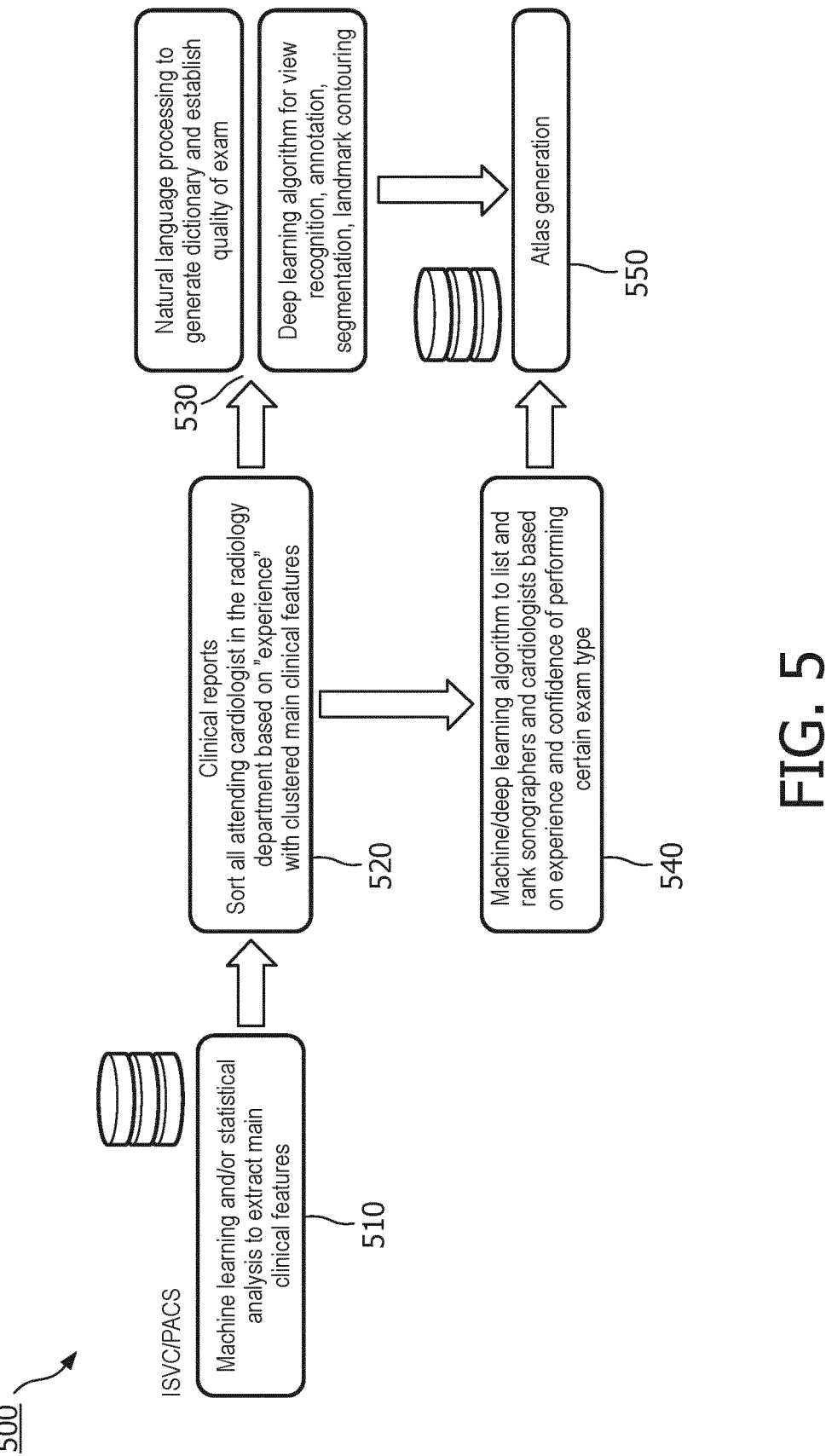
FIG. 5 is a schematic representation of a process for generating a sonogram atlas, in accordance with an embodiment.

Referring to FIG. 5, in one embodiment, is a schematic representation of a process 500 for generating a sonogram atlas. In this embodiment, at step 510 the process includes a machine learning algorithm that extracts clinical features from patient data, as described or otherwise envisioned herein. According to an embodiment, these clinical features can then be clustered. At step 520, radiograph interpreters in the facility or department are sorted, clustered, or ranked based on experience and can be associated with the clustered clinical features. Similarly, at step 540 of the process, sonograph users in the facility can be sorted, clustered, or ranked based on experience and/or on confidence performing one or more sonogram exam types. At step 530, the system can generate a database of findings and high-quality exams using NLP and can also utilize view recognition on images that were utilized to generate clinical reports. For example, the system can utilize a machine learning algorithm to learn annotation, segmentation, and landmarks contouring styles, such as preferred annotation, segmentation, and landmarks contouring styles for each of one or more radiograph interpreters. At step 550 of the method, omc or all of this information is then utilized to generate the sonogram atlas as described or otherwise envisioned herein.

According to an embodiment, the system standardizes the quality of imaging exams-such as preferred measurements-across an institution and helps sonograph users answer questions such as "what would the cardiologist do?," "which imaging view(s) should be selected for measurements?," and "are these images what a radiograph interpreter would prefer to use for a clinical report?," among other questions. For example, when measuring ejection fraction, a sonograph user (especially a novice) might get close to the imaging views that a cardiologist would prefer and/or select for measurements in clinical reports, yet the acquired loops/views might be cither low quality, or not similar enough to those existing in the pre-populated high-quality sonogram atlas. Hence, before the patient leaves the scanning room, sonograph users can request a "virtual cardiologist collaboration/consultation" where they can review the quality of their imaging exam, apply experienced cardiologists' measurements style and acquire higher quality loops/images, all without interrupting the cardiologists and by simply requesting a virtual consultation. The information for the virtual consultation can be pulled from the pre-populated sonogram atlas. Thus, when a sonograph user is asking for feedback during the ultrasound exam, the system can provide a virtual response and consultation without interrupting the cardiologist. The same concept can be applied to styles how cardiologists would perform certain measurements (e.g., placement of measurement markers relative to image features, contours, or gradients, and so on).

According to an embodiment, exam quality and user experience can be extracted from clinical reports using NLP, and this can be utilized to pre-populate reports for radiograph interpreters. If it is assumed that all sonograph users, especially novices, will submit their studies to a virtual consultation, their exams quality will be eventually standardized on an institutional level. Hence, cardiologists will most likely receive high-quality images and exams that will be very similar to the pre-populated sonogram atlas, by doing so we can utilize NLP and its dictionary to pre-populate cardiologist's reports.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "cither or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least once," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended. i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for providing information to a sonograph user using a sonogram atlas system, comprising:

providing a sonogram atlas comprising one or more sonogram preferences of each of a plurality of different radiograph interpreters, the sonogram preferences comprising at least one of a preferred view and a measurement for each of a plurality of sonogram types, wherein the sonogram atlas is generated by: (i) clustering a plurality of historical patients with sonogram data into similar clusters; (ii) identifying a plurality of different radiograph interpreters and a plurality of different sonograph users; (iii) sorting the sonogram data based on at least one of the identified plurality of different radiograph interpreters and an identified plurality of different sonograph users; (iv) generating the sonogram atlas from the sorted sonogram data; and (v) storing the generated sonogram atlas in storage;

receiving from a sonograph user, a request for information from the sonogram atlas about a sonogram being obtained by the sonograph user from a patient, wherein the request comprises one or more of demographic information about the patient, a type of exam, a reason for imaging, an identification of which of the plurality of different radiograph interpreters ordered the sonogram, and an identification of which of the one or more sonogram types was ordered by the identified radiograph interpreter(s);

retrieving from the sonogram atlas based on the request, the one or more sonogram preferences of the identified radiograph interpreter(s);

providing, to the sonograph user via a user interface of the sonogram atlas system, the retrieved one or more sonogram preferences of the identified radiograph interpreter(s); and adjusting, based on the provided retrieved information, a parameter of the sonogram being obtained by the sonograph user from the patient.

2. The method of claim 1, wherein providing the retrieved one or more sonogram preferences of the identified radiograph interpreter(s) to the sonograph user via the user interface comprises displaying one or more sonogram images.

3. The method of claim 1, wherein providing the retrieved one or more sonogram preferences of the identified radiograph interpreter to the sonograph user via the user interface comprises information about one or more sonogram preferences for each of a plurality of radiograph interpreters.

4. The method of claim 1, further comprising:

receiving, from the sonograph user after receiving the provided retrieved information, a request to communicate with the identified radiograph interpreter(s); and establishing, in response to the request, an electronic communication path between the sonograph user and the identified radiograph interpreter(s).

5. The method of claim 1, wherein:

clustering the plurality of historical patients with sonogram data into similar clusters is based on at least: (i) demographics for the patients and (ii) a sonogram type for the patient sonogram data;

identifying the plurality of different radiograph interpreters comprises, for each of the plurality of different radiograph interpreters, identifying years of experience, a radiology experience level;

identifying the plurality of different sonograph users comprises, for each of the plurality of different sonograph users, identifying years of experience, an imaging experience level and specialty; and sorting the sonogram data for the plurality of historical patients is based at least in part on the identified years of experience and experience level for the radiograph interpreter associated with the sonogram data, and based at least in part on the identified years of experience and experience level for the sonograph users associated with the sonogram data.

6. The method of claim 5, wherein the sonogram data associated with radiograph interpreters with more years of experience and higher experience level, and the sonogram data associated with sonograph users with more years of experience and higher experience level, is ranked higher or more reliable than sonogram data associated with radiograph interpreters with fewer years of experience and lower experience level, and the sonogram data associated with sonograph users with fewer years of experience and lower experience level in that imaging space, and further wherein the generated sonogram atlas comprises one or more sonogram preferences for each of the plurality of different radiograph interpreters based on the ranked sonogram data, the sonogram preferences comprising at least one of a preferred view and a measurement for each of a plurality of sonogram types.

7. The method of claim 5, wherein the method further comprises:

identifying high-quality sonogram data for each of the plurality of sonogram types among the sonogram data associated with the historical patients; and wherein the step of generating the sonogram atlas is further based in part on the identified high-quality sonogram data.

8. A system configured to provide information to a sonograph user, comprising:

a sonogram system configured to obtain a sonogram from a patient;

a sonogram atlas comprising one or more sonogram preferences of each of a plurality of different radiograph interpreters, the sonogram preferences comprising at least one of a preferred view and a measurement for each of a plurality of sonogram types, wherein the sonogram atlas is generated by: (i) clustering a plurality of historical patients with sonogram data into similar clusters; (ii) identifying a plurality of different radiograph interpreters and a plurality of different sonograph users; (iii) sorting the sonogram data based on at least one of the identified plurality of different radiograph interpreters and an identified plurality of different sonograph users; (iv) generating the sonogram atlas from the sorted sonogram data; and (v) storing the generated sonogram atlas in storage;

a user interface configured to receive, from a sonograph user, a request for information from the sonogram atlas about a sonogram being obtained by the sonograph user from a patient, wherein the request comprises one or more of demographic information about the patient, an identification of which of the plurality of different radiograph interpreters ordered the sonogram, imaging and scanning protocol, reason for imaging, views or measurements, and an identification of which of the one or more sonogram types was ordered by the identified radiograph interpreter(s); and a processor configured to: (i) retrieve, from the sonogram atlas based on the request, the one or more sonogram preferences of the identified radiograph interpreter; (ii) direct the user interface to provide the retrieved one or more sonogram preferences of the identified radiograph interpreter; (iii) adjust, based on the retrieved one or more sonogram preferences of the identified radiograph interpreter, a parameter of the sonogram being obtained by the sonograph user from the patient.

9. The system of claim 8, wherein providing the retrieved one or more sonogram preferences of the identified radiograph interpreter to the sonograph user via the user interface comprises displaying one or more sonogram images.

10. The system of claim 8, wherein providing the retrieved one or more sonogram preferences of the identified radiograph interpreter to the sonograph user via the user interface comprises information about one or more sonogram preferences for each of a plurality of radiograph interpreters.

11. The system of claim 8, wherein the processor is further configured to:

receive, from the sonograph user after receiving the provided retrieved information, a request to communicate with the identified radiograph interpreter; and establish, in response to the request, communication between the sonograph user and the identified radiograph interpreter.

12. The system of claim 11, wherein the user interface is configured to receive the request to communicate from the sonograph user, and further wherein the user interface is configured to facilitate the established communication between the sonograph user and the identified radiograph interpreter.

13. The system of claim 8, wherein the system is configured to receive, from the sonograph user based on the provided retrieved information, an adjustment of one or more parameters of the sonogram being obtained by the sonograph user from the patient.

14. The system of claim 8, wherein:

clustering the plurality of historical patients with sonogram data into similar clusters is based on at least: (i) demographics for the patients and (ii) a sonogram type for the patient sonogram data;

identifying the plurality of different radiograph interpreters comprises, for each of the plurality of different radiograph interpreters, identifying years of experience, a radiology experience level;

identifying the plurality of different sonograph users comprises, for each of the plurality of different sonograph users, identifying years of experience, an imaging experience level and specialty; and sorting the sonogram data for the plurality of historical patients is based at least in part on the identified years of experience and experience level for the radiograph interpreter associated with the sonogram data, and based at least in part on the identified years of experience and experience level for the sonograph users associated with the sonogram data.

15. The system of claim 14, wherein the sonogram data associated with radiograph interpreters with more years of experience and higher experience level, and the sonogram data associated with sonograph users with more years of experience and higher experience level, is ranked higher or more reliable than sonogram data associated with radiograph interpreters with fewer years of experience and lower experience level, and the sonogram data associated with sonograph users with fewer years of experience and lower experience level in that imaging space, and further wherein the generated sonogram atlas comprises one or more sonogram preferences for each of the plurality of different radiograph interpreters based on the ranked sonogram data, the sonogram preferences comprising at least one of a preferred view and a measurement for each of a plurality of sonogram types.

16. The system of claim 15, wherein the method further comprises:

identifying high-quality sonogram data for each of the plurality of sonogram types among the sonogram data associated with the historical patients; and wherein the step of generating the sonogram atlas is further based in part on the identified high-quality sonogram data.

17. A method for adjusting a parameter of a sonogram, comprising:

receiving, via a user interface of a sonogram atlas system, one or more sonogram preferences of an identified radiograph interpreter, wherein the one or more sonogram preferences of the identified radiograph interpreter are received by a method comprising:

providing a sonogram atlas comprising one or more sonogram preferences of each of a plurality of different radiograph interpreters, the sonogram preferences comprising at least one of a preferred view and a measurement for each of a plurality of sonogram types, wherein the sonogram atlas is generated by: (i) clustering a plurality of historical patients with sonogram data into similar clusters; (ii) identifying a plurality of different radiograph interpreters and a plurality of different sonograph users; (iii) sorting the sonogram data based on at least one of the identified plurality of different radiograph interpreters and an identified plurality of different sonograph users; (iv) generating the sonogram atlas from the sorted sonogram data; and (v) storing the generated sonogram atlas in storage;

receiving from a sonograph user, a request for information from the sonogram atlas about a sonogram being obtained by the sonograph user from a patient, wherein the request comprises one or more of demographic information about the patient, a type of exam, a reason for imaging, an identification of which of the plurality of different radiograph interpreters ordered the sonogram, and an identification of which of the one or more sonogram types was ordered by the identified radiograph interpreter;

retrieving from the sonogram atlas based on the request, the one or more sonogram preferences of the identified radiograph interpreter;

providing, to the sonograph user via the user interface of the sonogram atlas system, the retrieved one or more sonogram preferences of the identified radiograph interpreter; and adjusting, based on the provided retrieved information, a parameter of the sonogram being obtained by the sonograph user from the patient.

18. The method of claim 17, wherein:

clustering the plurality of historical patients with sonogram data into similar clusters is based on at least: (i) demographics for the patients and (ii) a sonogram type for the patient sonogram data;

identifying the plurality of different radiograph interpreters comprises, for each of the plurality of different radiograph interpreters, identifying years of experience, a radiology experience level;

identifying the plurality of different sonograph users comprises, for each of the plurality of different sonograph users, identifying years of experience, an imaging experience level and specialty; and sorting the sonogram data for the plurality of historical patients is based at least in part on the identified years of experience and experience level for the radiograph interpreter associated with the sonogram data, and based at least in part on the identified years of experience and experience level for the sonograph users associated with the sonogram data.

19. The method of claim 18, wherein the sonogram data associated with radiograph interpreters with more years of experience and higher experience level, and the sonogram data associated with sonograph users with more years of experience and higher experience level, is ranked higher or more reliable than sonogram data associated with radiograph interpreters with fewer years of experience and lower experience level, and the sonogram data associated with sonograph users with fewer years of experience and lower experience level in that imaging space, and further wherein the generated sonogram atlas comprises one or more sonogram preferences for each of the plurality of different radiograph interpreters based on the ranked sonogram data, the sonogram preferences comprising at least one of a preferred view and a measurement for each of a plurality of sonogram types.

20. The method of claim 19, wherein the method further comprises:

identifying high-quality sonogram data for each of the plurality of sonogram types among the sonogram data associated with the historical patients; and wherein the step of generating the sonogram atlas is further based in part on the identified high-quality sonogram data.

* * * * *